United States Patent
Lee et al.

(10) Patent No.: US 8,796,327 B2
(45) Date of Patent: Aug. 5, 2014

(54) METHOD FOR INHIBITING PRODUCTION OF CYTOKINES OF T HELPER CELL TYPE II AND/OR INHIBITING PRODUCTION OF CHEMOKINES USING BRAZILIN

(75) Inventors: Chen-Chen Lee, Taichung (TW); Chien-Neng Wang, Taichung (TW)

(73) Assignee: China Medical University, Taichung (TW)

( * ) Notice: Subject to any disclaimer, the term of this patent is extended or adjusted under 35 U.S.C. 154(b) by 627 days.

(21) Appl. No.: 12/850,857

(22) Filed: Aug. 5, 2010

(65) Prior Publication Data

US 2011/0213023 A1 Sep. 1, 2011

(30) Foreign Application Priority Data

Mar. 1, 2010 (TW) .............................. 99105793 A

(51) Int. Cl.
*A61K 31/35* (2006.01)
*A61K 31/352* (2006.01)

(52) U.S. Cl.
CPC .................................. *A61K 31/352* (2013.01)
USPC ............ 514/453; 514/451; 514/449; 514/183

(58) Field of Classification Search
None
See application file for complete search history.

(56) References Cited

U.S. PATENT DOCUMENTS

| 4,918,099 | A * | 4/1990 | Moon ............................ | 514/453 |
|---|---|---|---|---|
| 6,355,689 | B1 * | 3/2002 | Beswick et al. .............. | 514/665 |
| 6,620,848 | B2 * | 9/2003 | Beams et al. .................. | 514/562 |
| 2002/0010366 | A1 * | 1/2002 | Beams et al. .................. | 562/556 |
| 2004/0077639 | A1 * | 4/2004 | Manning ..................... | 514/227.5 |
| 2004/0087654 | A1 * | 5/2004 | Box et al. ........................ | 514/562 |

FOREIGN PATENT DOCUMENTS

WO  WO 2005063732 A1 * 7/2005 ........... C07D 311/24

OTHER PUBLICATIONS

"Cytokines and Cytokine Receptors" in Harrison's Principles of Internal Medicine, 17th Ed., McGraw-Hill Medical (New York), pp. 2025-2027 (2008).*
"Nitric oxide and asthma inflammation" by Barnes et al., Immunol. Today 16, 128-30 (1995).*
"Suppression of lipopolysaccharide-induced expression of inducible nitric oxide synthase by brazilin an RAW 264.7 macrophage cells" by Bae et al., Eur. J. Pharmacol. 513, 237-42 (2005).*
"Antiinflammatory Principles of *Caesalpinia sappan* Wood and of *Haematoxylon campechianum* Wood" by Hokino et al., Planta Med. 31, 414-20 (1977).*
Glaab, et al., "Repetitive measurements of pulmonary mechanics to inhaled cholinergic challenge in spontaneously breathing mice", J Appl Physiol 97:1104-1111 (2004).
Lee, et al., "Lentiviral-medicated GATA-3 RNAi Decreases Allergic Airway Inflammation and Hyperresponsiveness", The American Society of Gene Therapy, vol. 16, No. 1, 60-65 (2008).
Osawa, et al., "Predominant T helper type 2-inflammatory responses promote murine colon cancers", Int. J. Cancer, 118, 2232-2236 (2006).

* cited by examiner

*Primary Examiner* — Wu-Cheng Winston Shen
*Assistant Examiner* — Theodore R West
(74) *Attorney, Agent, or Firm* — Michael W. Ferrell; Ferrells, PLLC; Anna L. Kinney

(57) ABSTRACT

A method for inhibiting the production of cytokines of T helper cell type II (Th2 cell) and/or inhibiting the production of chemokines in a mammal is provided, wherein the method comprises administrating to the mammal an effective amount of an active component selected from a group consisting of a compound of formula (I), pharmaceutically acceptable salts and esters of the compound, and combinations thereof:

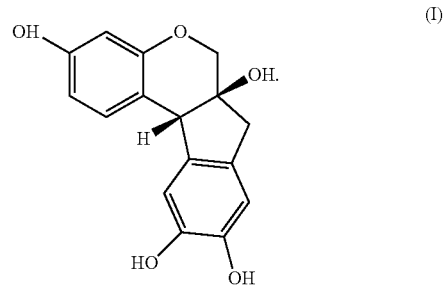

(I)

4 Claims, 8 Drawing Sheets

C: Control group

METHOD FOR INHIBITING PRODUCTION OF CYTOKINES OF T HELPER CELL TYPE II AND/OR INHIBITING PRODUCTION OF CHEMOKINES USING BRAZILIN

RELATED APPLICATION

This application claims priority to Taiwan Patent Application No. 099105793 filed on Mar. 1, 2010, the disclosure of which is incorporated herein in its entirety by reference.

BACKGROUND OF THE INVENTION

1. Field of the Invention

The present invention relates to use of brazilin in inhibiting the production of cytokines of T helper cell type II (Th2 cell) and/or inhibiting the production of chemokines.

2. Descriptions of the Related Art

Allergic diseases are a kind of common diseases. Mild allergic conditions include those caused by foods or by insect bites, while severe allergic conditions include atopic dermatitis, allergic rhinitis, asthma, and so on. In the last decades, industrialization and development of civilization have caused environmental pollution and changes in people's diet habits. As a consequence, both incidence and severity of allergic diseases are increasing all over the world.

Currently, treatment of allergic diseases still mainly relies on control by medicines. Although anti-allergic medicines, such as corticosteroids, anti-histamines, and anti-leukotrienes, have already been available in the market, there is still around 5% of allergy patients cannot have their conditions got effectively controlled by taking such medicines. Furthermore, each of these medicines has different side effects. For example, the corticosteroids may cause gain of body weight, edema, hypertension, potassium loss, and the like; the anti-histamines may cause lethargy, headache, blurred vision, and the like; and the anti-leukotrienes may cause gastrointestinal discomfort, and so on. Moreover, the greatest problem with these medicines is that, once the patient stops taking the medicines, the allergy symptoms (e.g., inflammatory responses) will relapse within a short time period, so these medicines cannot be used to provide a long-term or long-lasting effect.

On the other hand, allergic diseases may also be treated by taking traditional Chinese medicines. However, traditional Chinese medicines for treating allergic diseases currently available in the market are mostly compound medicines, which still have many problems in terms of medicine preparation and control of dosage and efficacy.

In view of the aforesaid drawbacks of treating allergic diseases with western medicines and traditional Chinese medicines, a need still remains in the art for a substance or pharmaceutical composition that can treat allergic diseases effectively with less side effect and that is easy to prepare.

The present invention is just made to satisfy this need. Through related in vivo and in vitro experiments, the inventors of the present invention confirmed that brazilin can inhibit the production of cytokines of T helper cells type II (Th2 cell) and the production of chemokines, and can deliver a long-term effect of controlling or curing allergic diseases by regulating the fundamental immunologic mechanism.

SUMMARY OF THE INVENTION

An objective of the present invention is to provide a method for inhibiting the production of cytokines of T helper cells type II (Th2 cell) and/or inhibiting the production of chemokines in a mammal, comprising administrating to the mammal an effective amount of an active component selected from a group consisting of a compound of formula (I), pharmaceutically acceptable salts and esters of the compound, and combinations there of:

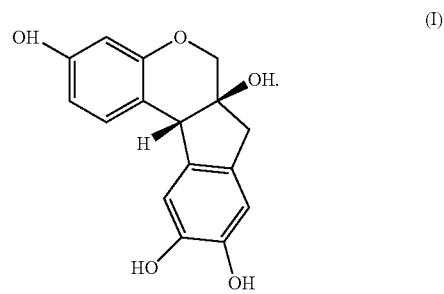 [SMILES: Oc1ccc2c(c1)OC[C@]1(O)Cc3cc(O)c(O)cc3[C@H]21]

(I)

The detailed technology and preferred embodiments implemented for the subject invention are described in the following paragraphs accompanying the appended drawings for people skilled in this field to well appreciate the features of the claimed invention.

DESCRIPTION OF THE PREFERRED EMBODIMENT

Figure 1:
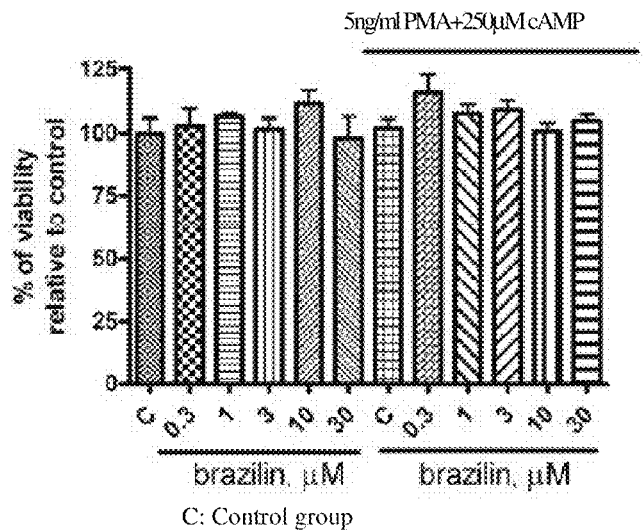
FIG. 1 shows a histogram of cell viability of EL-4 T lymphoma cells.

Unless otherwise stated herein, the terms "a (an)", "the" or the like used in this specification (especially in the Claims hereinafter) shall be understood to encompass both the singular form and the plural form. Furthermore, the phrase "production of cytokines" shall be understood to encompass generation, expression, and release of cytokines, and the phrase "production of chemokines" shall be understood to encompass generation, expression, and release of chemokines.

T cells play a key role in the immunologic mechanism, and depending on species of cytokines they secrete, can differentiate into two kinds of cells: T helper cells type I (i.e., Th1 cells), which can produce interferon-γ (IFN-γ) and interleukin-2 (IL-2); and T helper cells type II (i.e., Th2 cells), which can produce interleukin-4 (IL-4), interleukin-5 (IL-5), interleukin-6 (IL-6), and interleukin-10 (IL-10). The Th1 cells can help killer cells and, by secreting IFN-γ, activate macrophages to promote cellular immune responses; and the Th2 cells can assist B cells in producing anaphylactic antibodies IgE and, by secreting IL-4 and IL-5, activate mast cells or eosinophils to secrete inflammatory mediators including histamines, leukotrienes, postaglandines, and so on. The Th1 cells and the Th2 cells have an antagonism relationship with each other: IFN-γ released by the Th1 cells can inhibit the Th2 cells, while IL-4 or IL-10 released by the Th2 cells can inhibit the Th1 cells from generating IFN-γ.

Therefore, interaction of the Th1 cells and the Th2 cells has an influence on physiological immune responses and is very closely related to a lot of diseases. For example, it is already known that Th2 cells with excessively high activity may cause allergy and consequently cause allergic diseases, e.g., airway allergy which may lead to allergic cough or allergic asthma; additionally, as has been proven in some references, enhancement of immune responses of the Th2 cells may promote carcinogens to induce occurrence of colon cancer (see Osawa et al., Predominant T helper type 2-inflammatory responses promote murine colon cancers, *Int J Cancer*, 2006, 118(9): 2232-6, which is incorporated herein in its entirety by reference). On the other hand, excessively high activity of the Th1 cells may cause dysfunction of autoimmunity. Hence, if the immunologic balance between the Th1 cells and the Th2 cells can be regulated to maintain activities of the two kinds of cells at their respective normal levels, autoimmune diseases can be cured, allergic diseases (including allergic cough or allergic asthma) can be improved, and colon cancers can be inhibited.

Furthermore, in the immunologic mechanism, cytokines secreted by immunocytes also comprise chemokines which can be categorized into α-chemokines (CXC chemokines), β-chemokines (CC chemokines), γ-chemokines (C chemokines), and δ-chemokines ($CX_3C$ chemokines) depending on molecular structures thereof. The chemokines are chemotactic, and can selectively (or exclusively) attract different immunocytes to specific sites to produce an immune response; for example, the two most common chemokines, i.e., the α-chemokines and the β-chemokines, can attract neutrophils and eosinophils respectively.

Medicines that are known to treat allergic diseases include corticosteroids, anti-histamines, and anti-leukotrienes, all of which acts on inflammatory mediators secreted by mast cells or eosinophils; in other words, these medicines function to inhibit and regulate the back-end (downstream) immune responses of the Th2 cells, but not to address the fundamental cause of the allergy.

The inventors of the present invention found that, brazilin has an activity to inhibit the production of cytokines of Th2 cells, so it can be used to inhibit the production of cytokines of Th2 cells and inhibit and regulate the immune response of Th2 cells at an early stage, thereby to deliver an effect of inhibiting the fundamental cause of the allergic diseases. On the other hand, the inventors of the present invention also found that, brazilin has an activity to inhibit the production of chemokines, especially the production of β-chemokines. As described above, β-chemokines can attract eosinophils which are related to the immune responses of Th2 cells. Therefore, brazilin and/or pharmaceutically acceptable salts and/or esters thereof may be used to inhibit the immune responses of Th2 cells by inhibiting the production of β-chemokines, so as to treat the allergic diseases.

Accordingly, the present invention provides a method for inhibiting the production of cytokines of Th2 cells and/or inhibiting the production of chemokines in a mammal, comprising administrating to the mammal an effective amount of an active component, and the active component is selected from a group consisting of a compound of formula (I), pharmaceutically acceptable salts and esters of the compound, and combinations thereof:

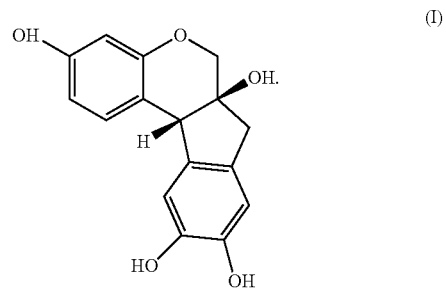 [SMILES: Oc1ccc2c(c1)OC[C@]1(O)Cc3cc(O)c(O)cc3[C@H]21]

(I)

Here, the compound of formula (I) is just brazilin, which is obtained from plants of the Caesalpiniaceae family and often used for cloth dyeing and cell staining.

The method of the present invention can inhibit the production of at least one of IL-4 and IL-5 cytokines of Th2 cells and/or inhibit the production of β-chemokines. The brazilin can inhibit expression of proteins and mRNA of IL-4 and IL-5 by inhibiting the expression of transcription factors c-maf of IL-4 and transcription factors GATA binding protein 3 (GATA-3) of IL-5. Especially, the brazilin can inhibit the production of eotaxin (CCL11). Eotaxin is a kind of β-chemokines, which has higher selectivity to eosinophils than other β-chemokines (e.g., CCL5). Hence, by inhibiting the production of eotaxins, the method of the present invention can inhibit allergic immune responses more exclusively.

Because the method of the present invention has an efficacy of inhibiting the production of cytokines of Th2 cells and/or the production of β-chemokines, allergic diseases can be treated by regulating the immune responses of Th2 cells. As proved by animal model experiments on mice with asthma diseases, the brazilin can effectively alleviate symptoms of airway allergy, including inhibiting airway inflammation and decreasing airway resistance. This demonstrates that the method of the present invention can be used for treating allergic asthma.

The present invention also provides uses of the compound of formula (I), and/or the pharmaceutically acceptable salts and/or esters thereof in the manufacture of a medicament, wherein the medicament is used to inhibit the production of cytokines of Th2 cells and/or inhibit the production of chemokines. Particularly, the medicament is used to inhibit the production of at least one of IL-4 and IL-5 cytokines and the production of β-chemokines, so it has the efficacy of treating allergic diseases, inhibiting airway inflammation, decreasing airway resistance, and treating allergic asthma, and the like.

The medicament of the present invention may be administrated in any appropriate ways, for example but not limited to, oral administration, subcutaneous administration, or intravenous administration. This medicament can be used for veterinary and human use either alone or in combination with a medical adjuvant.

Taking manufacture of a medicament suitable for oral administration as an example, adjuvants that will not adversely affect activity of the compound of formula (I) may be incorporated in the medicament of the present invention, for example, a solvent, an oily solvent, a thinner, a stabilizer, an absorption retarder, a disintegrant, an emulsifier, a binder, a lubricant, a moisture absorbent, or the like. For example, the solvent may be selected from a group consisting of water and saccharose solutions; the thinner may be selected from a group consisting of lactose, starch, and microcrystalline cellulose; the absorption retarder may be selected from a group consisting of chitosan and glycosaminoglycans; the lubricant may be magnesium carbonate; the oily solvent may be selected from a group consisting of vegetable oils and animal oils, such as olive oil, sunflower oil, cod-liver oil, etc. By use of conventional processes, the medicament of the present invention can be formulated into a form suitable for oral administration, for example, into a form of tablets, capsules, granules, pulvis, fluid extracts, solutions, syrups, suspensions, emulsions, tinctures, and so on.

When a medicament form suitable for subcutaneous administration or intravenous administration is desired, one or more components such as a solubilizer, an emulsifier, or other adjuvants may be incorporated in the medicament of the present invention to form an intravenous fluid, an intravenous emulsion, an injection, a dry powder injection, a suspension injection, a dry powder suspension injection, or the like. Solvents that may be adopted include, for example, water, normal saline, alcohols (e.g., ethanol, propanol, or glycerin), sugar solutions (e.g., glucose solutions or mannose solutions), or combinations thereof.

The medicament of the present invention may optionally further comprise additives such as a flavoring agent, a color toner, and a coloring agent to improve the mouth feel and visual experience when the resulting medicament is taken; also, a preservative, an antiseptic, an antimicrobial, an antimycotic, or the like may be added at a reasonable amount to improve storability of the resulting medicament.

Furthermore, one or more other active components may be optionally incorporated in the medicament of the present invention to further enhance efficacy of the medicament or to enhance flexibility in administration and formulation of the medicament formulary. For example, one or more of the following active components may be incorporated in the medicament of the present invention: corticosteroids, antihistamines, and anti-leukotrienes as well as other active components, provided that the active component(s) will not adversely affect the efficacy of the compound of formula (I).

Depending on demands of the subject who receives the administration, the medicament of the present invention may be administrated once every day, several times every day, or once every several days. For example, when used in a human body for treating allergic asthma, the medicament may be administrated at an amount of, calculated as the compound of formula (I), about 0.25 µg/kg-body weight per day to about 2.5 µg/kg-body weight per day. Herein, the unit "µg/kg-body weight" refers to an amount of the medicament to be administrated per kg of body weight. Preferably, the amount of the medicament, calculated as the compound of formula (I), is about 0.30 µg/kg-body weight per day to about 2.5 µg/kg-body weight per day. However, for patients with acute conditions (e.g., for patients with acute asthma), the amount of administration may be increased by several or several tens of times depending on practical conditions.

Hereinafter, the present invention will be further illustrated with reference to the following examples. However, these examples are only provided for illustrate purpose, but not to limit the scope of the present invention.

Example 1

In Vitro Experiments

Experiment A: Cell Culture

In this example, effect of the brazilin on cytokines of Th2 cells is evaluated. Chemicals and reagents used are: brazilin commercially available from EMD Chemical Inc., Darmstadt, Germany; lipopolysaccharides (LPS) from *Escherichia coli* 055:B5, ovalbumin (OVA), phorbol-12-myristate 13-acetate (PMA), and cyclic adenosine monophosphate (cAMP) commercially available from Sigma Chemical, St. Louis, Mo., America; RPMI-1640 culture medium, DMEM culture medium. Hank's balanced salt solution (HBSS). Penicillin, streptomycin, L-glutamate, and fetal bovine serum (FBS) commercially available from Invitrogen, Carlsbad, Calif., America.

First, in an incubator containing 5 vol % of $CO_2$ at 37° C., EL-4 mouse T lymphoma cells (commercially available from ATCC, Manassas, Va., America) were cultured in the DMEM culture medium (containing 10 wt % of thermally deactivated FBS), and were sub-cultured at a ratio of 1:3.

Then, at a density of $5 \times 10^5$ counts/ml, the T lymphoma cells were bred in a six-well culture dish, and at the $0^{th}$ minute, brazilin of different concentrations (0.3, 1, 3, 10, or 30 micromole (µM)) was added into the cell culture solution at an amount of 1 µl/ml-cell culture solution. Then, the cells were put into the incubator to be cultured therein. 30 minutes later, at an amount of 1 µl/ml-cell culture solution, 5 µg/ml PMA and cAMP at a 250 mmol concentration were added to the cell culture solution to stimulate the expression of IL-4 and IL-5 of the T lymphoma cells. During the process of cell culture, the trypan blue exclusion assay was employed to observe effect of the brazilin on the cell viability, results of which are shown in Table 1 and FIG. 1.

TABLE 1

| Concentration of brazilin (µM) | *Cell viability (%) |
|---|---|
| 0 | 100.0 ± 5.738 |
| 0.3 | 102.8 ± 6.895 |
| 1 | 106.5 ± 1.190 |
| 3 | 101.5 ± 4.226 |
| 10 | 111.5 ± 5.126 |
| 30 | 98.17 ± 8.439 |
| PMA + cAMP | 102.0 ± 3.416 |
| 0.3 | 115.9 ± 6.968 |
| 1 | 107.4 ± 3.829 |
| 3 | 109.0 ± 3.764 |
| 10 | 100.8 ± 3.257 |
| 30 | 104.7 ± 2.495 |

*Mean ± standard deviation, and the sample number ≥3.

As can be seen from Table 1 and FIG. 1, the brazilin had no effect on the growth of EL-4 T lymphoma cells, which means that it has no cytotoxicity.

Experiment B: Analysis of Proteins

At 4° C., the T lymphoma cells obtained from Experiment A were centrifugally rotated at a rotational speed of 1000 rpm and at 4° C. for 5 minutes, and the supernatant was collected and analyzed for cytokines.

Figure 2:
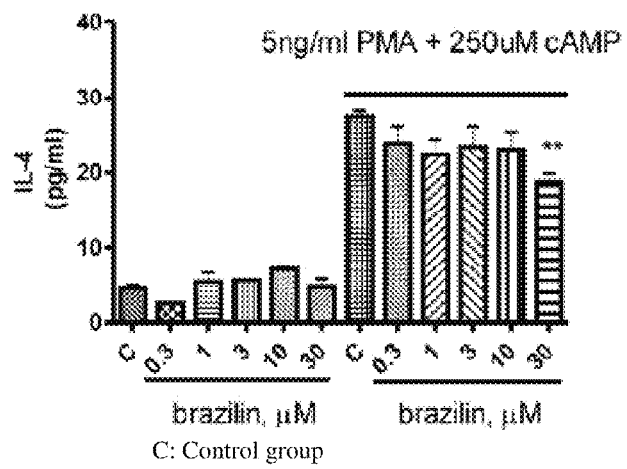
FIG. 2 shows a histogram of IL-4 concentrations in EL-4 T lymphoma cells.
Figure 3:
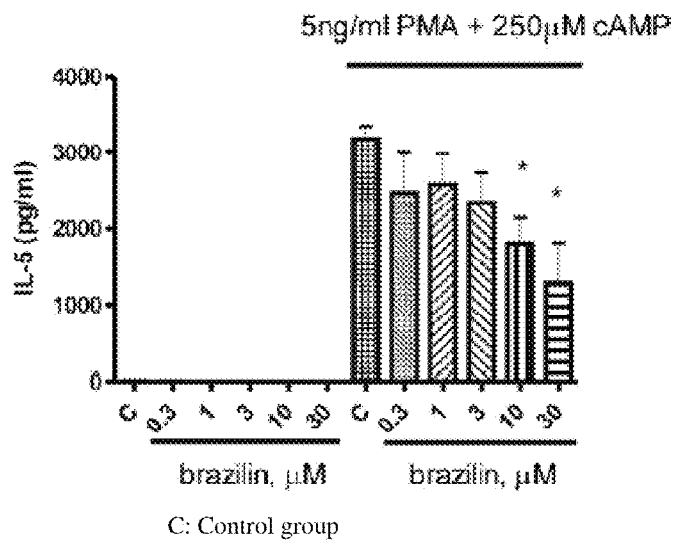
FIG. 3 shows a histogram of IL-5 concentrations in EL-4 T lymphoma cells.
Figure 4:
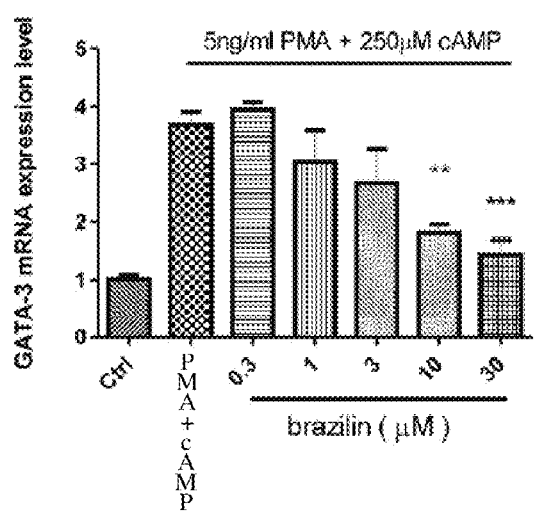
FIG. 4 shows a histogram of mRNA concentrations of GATA-3 in EL-4 T lymphoma cells.
Figure 5:
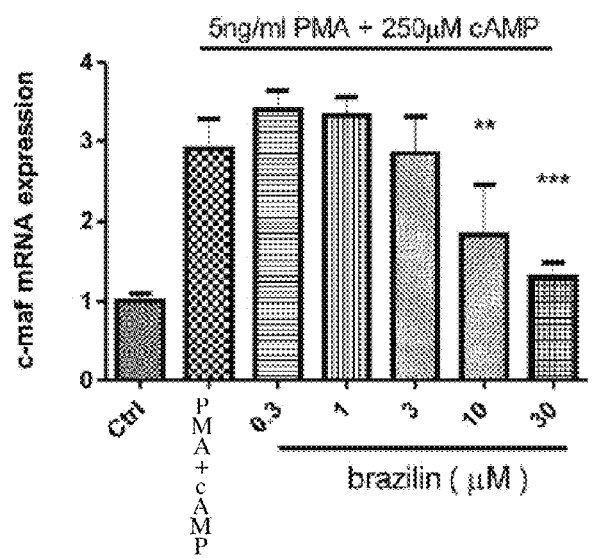
FIG. 5 shows a histogram of mRNA concentrations of c-maf in EL-4 T lymphoma cells.
Figure 6:
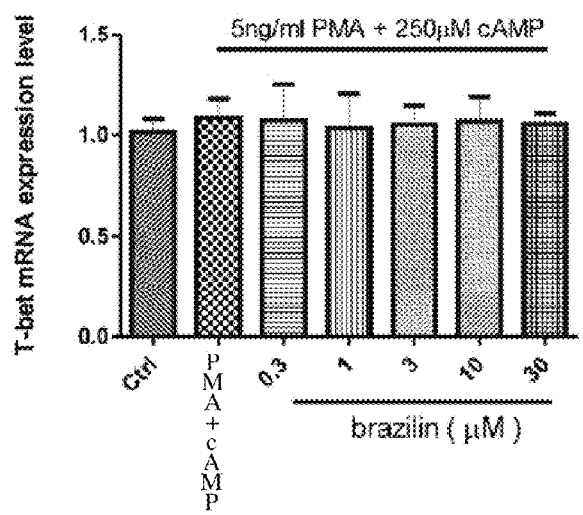
FIG. 6 shows a histogram of mRNA concentrations of T-bet in EL-4 T lymphoma cells.
Figure 7:
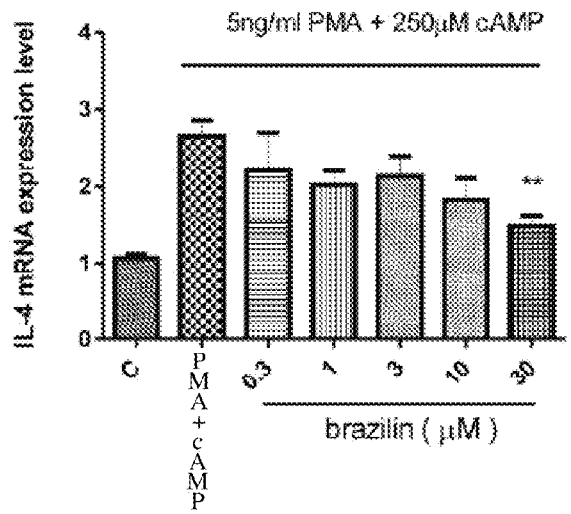
FIG. 7 shows a histogram of mRNA concentrations of IL-4 in EL-4 T lymphoma cells.
Figure 8:
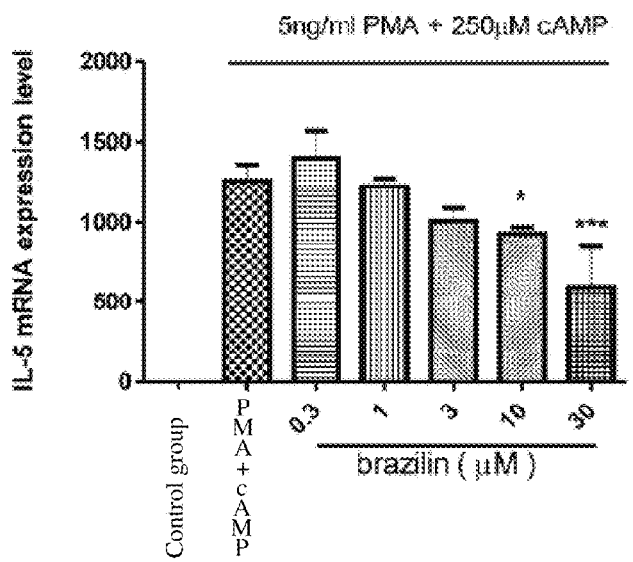
FIG. 8 shows a histogram of mRNA concentrations of IL-5 in EL-4 T lymphoma cells.

An enzyme-linked immunosorbent assay (ELISA) kit (commercially available from R&D Systems, Inc., America) was used to analyze the expression of IFN-γ, IL-4, IL-5, and eotaxin cytokines in the aforesaid supernatant, results of which are shown in Table 2, Table 3, FIG. 2, and FIG. 3.

In Experiment B and the following Experiment C, all experimental data are presented in form of "mean±standard deviation", and statistical discrepancy was analyzed by means of the One-way ANOVA and Newman-keuls post-hoc tests, in which it is considered that there is statistical discrepancy if $p<0.05$.

TABLE 2

| Concentration of brazilin (μM) | Concentration of IL-4 (pico-gram/ml) |
| --- | --- |
| Control group | 4.541 ± 0.3480 |
| 0.3 | 2.569 ± 0.1160 |
| 1 | 5.353 ± 1.276 |
| 3 | 5.469 ± 0.1160 |
| 10 | 7.093 ± 0.3480 |
| 30 | 4.715 ± 0.9859 |
| PMA + cAMP Control group | 27.42 ± 0.8208 |
| 0.3 + .PMA + cAMP | 23.93 ± 2.214 |
| 1 + PMA + cAMP | 22.49 ± 1.969 |
| 3 + PMA + cAMP | 23.45 ± 2.693 |
| 10 + PMA + cAMP | 23.13 ± 2.297 |
| 30 + PMA + cAMP | 18.71 ± 1.206 *** |

As compared to the PMA + cAMP control group,
* $p < 0.05$,
** $p < 0.01$,
*** $p < 0.001$,
mean ± standard deviation, and the sample number ≥3.

TABLE 3

| Concentration of brazilin (μM) | Concentration of IL-5 (pico-gram/ml) |
| --- | --- |
| Control group | 9.881 ± 2.473 |
| 0.3 | 5.925 ± 3.462 |
| 1 | 0.2422 ± 0.2422 |
| 3 | 0.2422 ± 0.2422 |
| 10 | 1.474 ± 0.9891 |
| 30 | 0.0 ± 0.0 |
| PMA + cAMP Control group | 3179 ± 167.9 |
| 0.3 + PMA + cAMP | 2480 ± 515.9 |
| 1 + PMA + cAMP | 2580 ± 402.8 |
| 3 + PMA + cAMP | 2345 ± 392.6 |
| 10 + PMA + cAMP | 1809 ± 337.9 * |
| 30 + PMA + cAMP | 1292 ± 531.6 * |

As compared to the PMA + cAMP control group,
* $p < 0.05$,
** $p < 0.01$,
*** $p < 0.001$,
mean ± standard deviation, and the sample number ≥3.

As can be seen from Table 2, Table 3, FIG. 2, and FIG. 3, the brazilin inhibited the expression of proteins of IL-4 and IL-5 cytokines of Th2 cells.

Experiment C: mRNA Analysis

Expression of mRNA of IL-4, IL-5, GATA-3, c-maf, and T-bet were analyzed in a quantitative way through real-time polymerase chain reaction (PCR) by extracting RNA in the cells obtained in Experiment A (using an RNA purifying kit), converting the RNA into cDNA through reverse transcription, and using an ABI PRISM 7700 sequence detector (Applied Biosystems, Foster City, Calif., America) to analyze the gene expression of mRNA. The PCR was carried out under the following conditions: 50° C., 2 minutes; 95° C., 10 minutes; 60° C., 1 minute; then repeating this cycle forty times. A threshold cycle (or referred to as Ct) was used to represent the expression level of each gene, and an expression level of hypoxanthine-guanine phosphoribosy transferase (HPRT) genes of the endogenous control group was used for correction of the expression level of mRNA. The results are shown in Tables 4 to 8 and FIGS. 4 to 8.

TABLE 4

| Concentration of brazilin (μM) | Expression level of IL-4 mRNA |
| --- | --- |
| Control group | 1.066 ± 0.04998 |
| PMA + cAMP | 2.662 ± 0.1964 |
| 0.3 | 2.228 ± 0.4786 |
| 1 | 2.028 ± 0.1794 |
| 3 | 2.136 ± 0.2671 |
| 10 | 1.835 ± 0.2712 |
| 30 | 1.478 ± 0.1441** |

As compared to the PMA + cAMP control group,
*$p < 0.05$,
**$p < 0.01$,
***$p < 0.001$,
mean ± standard deviation, and the sample number ≥3.

TABLE 5

| Concentration of brazilin (μM) | Expression level of IL-5 mRNA |
| --- | --- |
| Control group | 1.053 ± 0.08942 |
| PMA + cAMP | 1261 ± 97.18 |
| 0.3 | 1397 ± 172.2 |
| 1 | 1225 ± 47.23 |
| 3 | 1009 ± 77.66 |
| 10 | 926.2 ± 40.70 * |
| 30 | 594.8 ± 252.9 *** |

As compared to the PMA + cAMP control group,
* $p < 0.05$,
** $p < 0.01$,
*** $p < 0.001$,
mean ± standard deviation, and the sample number ≥3.

TABLE 6

| Concentration of brazilin (μM) | Expression level of GATA-3 mRNA |
| --- | --- |
| Control group | 1.018 ± 0.07240 |
| PMA + cAMP | 3.699 ± 0.2105 |
| 0.3 | 3.960 ± 0.1234 |
| 1 | 3.036 ± 0.5622 |
| 3 | 2.663 ± 0.6056 |
| 10 | 1.812 ± 0.1538** |
| 30 | 1.434 ± 0.2530*** |

As compared to the PMA + cAMP control group,
*$p < 0.05$,
**$p < 0.01$,
***$p < 0.001$,
mean ± standard deviation, and the sample number ≥3.

TABLE 7

| Concentration of brazilin (μM) | Expression level of c-maf mRNA |
| --- | --- |
| Control group | 1.004 ± 0.02337 |
| PMA + cAMP | 2.913 ± 0.1499 |
| 0.3 | 3.388 ± 0.2410 |
| 1 | 3.318 ± 0.1177 |

TABLE 7-continued

| Concentration of brazilin (μM) | Expression level of c-maf mRNA |
|---|---|
| 3 | 2.846 ± 0.2632 |
| 10 | 1.826 ± 0.6278** |
| 30 | 1.302 ± 0.1868*** |

As compared to the PMA + cAMP control group,
*p < 0.05,
**p < 0.01,
***p < 0.001,
mean ± standard deviation, and the sample number ≥3.

TABLE 8

| Concentration of brazilin (μM) | Expression level of T-bet mRNA |
|---|---|
| Control group | 1.017 ± 0.06221 |
| PMA + cAMP | 1.084 ± 0.09578 |
| 0.3 | 1.073 ± 0.1762 |
| 1 | 1.036 ± 0.1666 |
| 3 | 1.052 ± 0.09226 |
| 10 | 1.068 ± 0.1171 |
| 30 | 1.054 ± 0.05147 |

As compared to the PMA + cAMP control group,
* p < 0.05,
** p < 0.01,
*** p < 0.001,
mean ± standard deviation, and the sample number ≥3.

As can be seen from Tables 4 to 8 and FIGS. 4 to 8, the brazilin inhibited the expression of mRNA of IL-4 and IL-5 cytokines of Th2 cells. Furthermore, the brazilin inhibited the expression of mRNA of transcription factors c-maf of IL-4 and transcription factors GATA-3 of IL-5, but did not inhibit the expression of mRNA of transcription factors T-bet of INF-γ. This demonstrates that the brazilin inhibits the production of cytokines of Th2 cells but does not inhibit the production of cytokines of Th1 cells. These results reveals that the brazilin can inhibit excessively high immune responses of Th2 cells in the immunologic balance between the Th1 cells and the Th2 cells, so it can be used for treatment of allergic diseases.

Example 2

In Vivo Experiments

Experiment D: Animal Model Test on Mice with Asthma

In Example 2, mice with asthma were used to conduct in vivo experiments, and ovalbumin (OVA) was used as an allergen.

Figure 9:
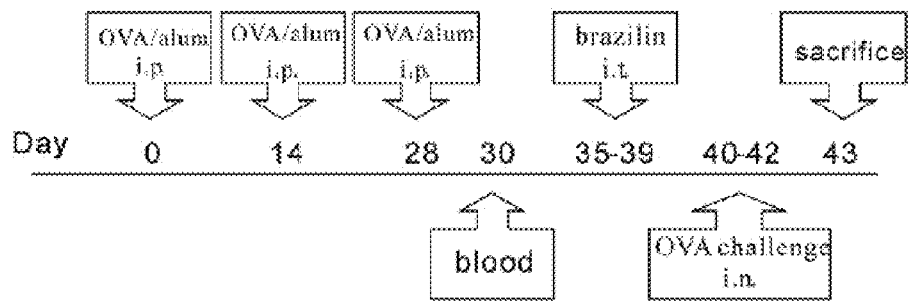
FIG. 9 shows a flowchart of an animal model test on mice with asthma.

The mice were sensitized (or challenged) according to the steps shown in FIG. 9 (see Lee et al., Lentiviral-mediated GATA-3 RNAi decreases allergic airway inflammation and hyperresponsiveness. *Molecular Therapy*, 2008; 16:60-65, which is incorporated herein in its entirety by reference). First, 50 μg OVA (using 2 mg alumina (Alum, Alumlmuject, Pierce Chemical, Rockford, Ill., USA) as an adjuvant) was injected into six to eight-week-old BALB/c female mice (from National Laboratory Animal Center, Taiwan) by intraperitoneal injection (i.p.). At $0^{th}$, $14^{th}$, and $28^{th}$ day, the mice were injected with OVA at the same dosage. Before the administration of OVA at the forty-first and the forty-second days, different dosages of brazilin (high dose: 430 μg/mice; low dose: 43 μg/mice) were administered to the mice by intraperitoneal injection (i.p.) or intratracheal instillation (i.t.). During the fortieth to the forty-second days, 100 μg OVA was dissolved in 40 μl PBS, and was administrated to the mice by intranasal instillation (i.n.) (once everyday, for three days). At the forty-third day, airway hyperresponsiveness of the mice was observed. At the forty-sixth day, the mice were sacrificed and used to conduct the following Experiments E to G During the above procedure, it was observed if any toxicity response arises after the administration of brazilin to the mice. In this experiment, the mice administrated with OVA were used as a positive control, and the mice not administrated with OVA were used as a negative control.

Experiment E: Histopathological Examination

In Experiment D, after 24 hours from the last administration of OVA into the noses of the mice, the mice were sacrificed, and the blood was collected from the orbital cavities of the mice. Then, a cannula was immediately inserted into the bronchi of the mice, and the lungs of the mice were washed with a 1 ml HBSS buffer solution containing no calcium and magnesium ions three times, and a bronochial alveolar lavage fluid is collected. The fluid was centrifuged at 4° C. and with a revolution speed of 400 g for 10 minutes. Cells obtained after the centrifugation were re-suspended in a 1 ml HBSS buffer solution, and the total cell number was counted with a hemocytometer.

Then, the cells were fixed on a glass sheet in a way of cytocentrifuged preparations, and the Liu's stain (see Lee et al., Lentiviral-mediated GATA-3 RNAi decreases allergic airway inflammation and hyperresponsiveness. *Molecular Therapy*. 2008; 16:60-65, which is incorporated herein in its entirety by reference) was carried out to calculate the number of various kinds of cells. The cell number was calculated by counting the number of macrophages, lymphocytes, eosinophils, and neutrophils in 300 cells respectively. The cells were categorized according to their standard morphology, and the invasion of inflammatory cells into the lungs was observed. The results are shown in Tables 9 to 12 and FIG. 10.

Figure 11:
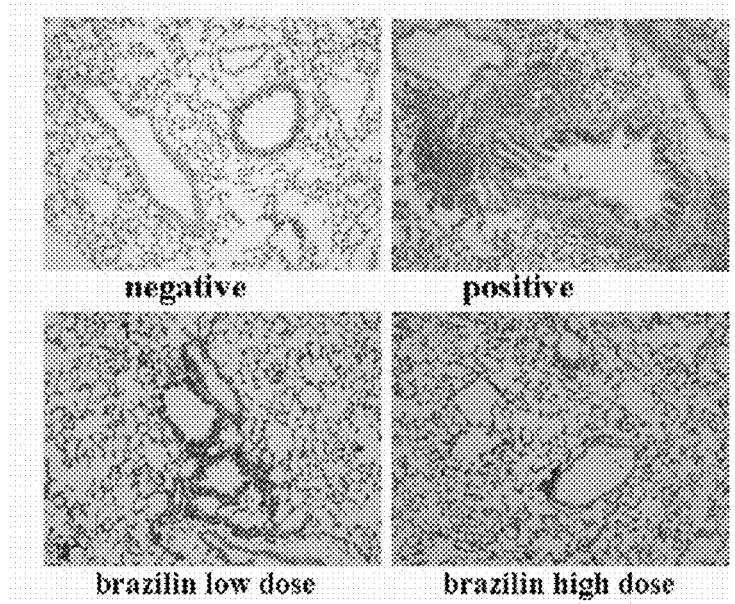
FIG. 11 shows H&E stained lung tissue slices of BALB/c mice.
Figure 12:
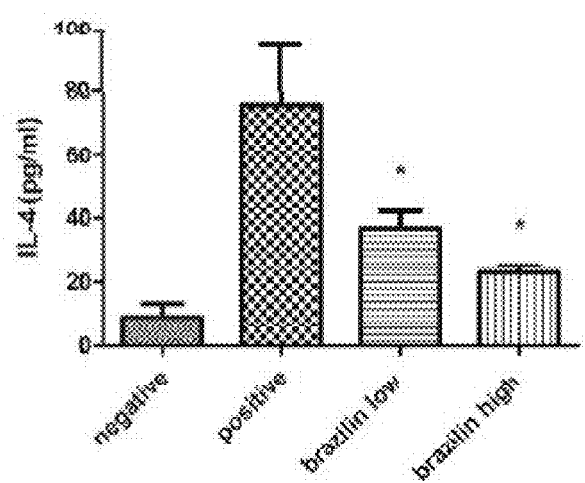
FIG. 12 shows a histogram of IL-4 concentrations in the bronochial alveolar lavage fluids of the BALB/c mice.
Figure 13:
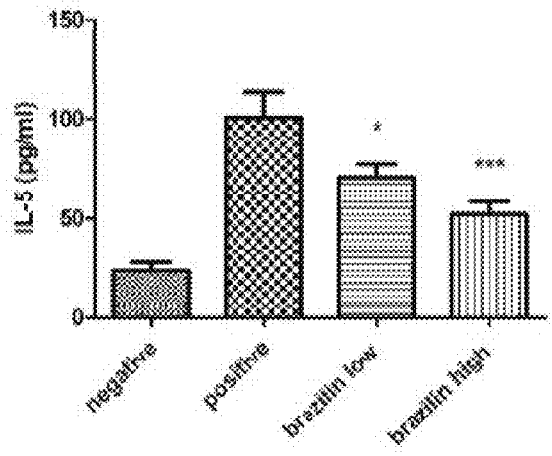
FIG. 13 shows a histogram of IL-5 concentrations in the bronochial alveolar lavage fluids of the BALB/c mice.
Figure 14:
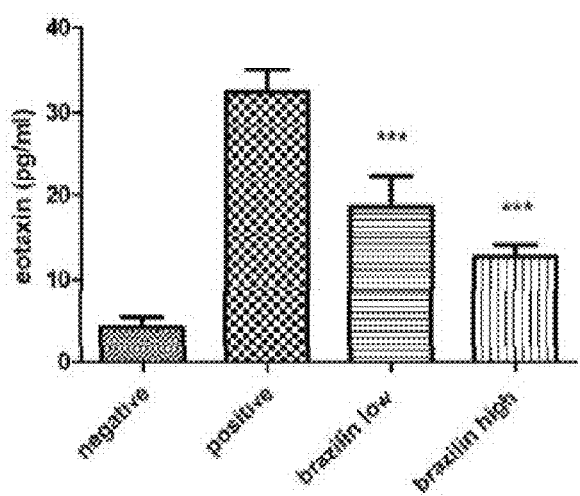
FIG. 14 shows a histogram of eotaxin chemokine concentrations in the bronochial alveolar lavage fluids of the BALB/c mice.
Figure 15:
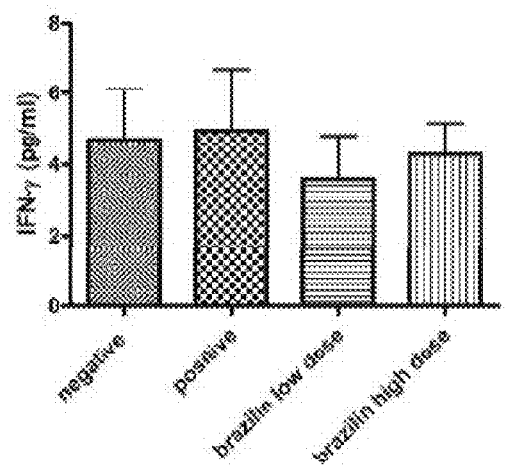
FIG. 15 shows a histogram of IFN-γ concentrations in the bronochial alveolar lavage fluids of the BALB/c mice.

Histopathological examinations were carried out by taking the lungs out of the mice right after collecting the bronochial alveolar lavage fluid, and fixing the lungs with neutral formalin. After the lung tissues were embedded by paraffin wax, they were cut into slices with a thickness of 5 μm, and the slices were stained with hematoxylin/eosin (H&E), and the invasion of inflammatory cells (or immunocytes) was observed under a microscope. The results are shown in FIG. 11 (the micrograph amplified by 200-fold).

TABLE 9

| Concentration of brazilin (μM) | Number of macrophages (×$10^4$) |
|---|---|
| Negative control | 5.381 ± 2.053 |
| Positive control | 38.46 ± 6.110 |
| Low dose | 41.67 ± 6.885 |
| High dose | 34.25 ± 4.970 |

TABLE 10

| Concentration of brazilin (μM) | Number of eosinophils (×$10^4$) |
|---|---|
| Negative control | 1.351 ± 1.101 |
| Positive control | 32.36 ± 2.800 |
| Low dose | 21.39 ± 1.491* |
| High dose | 10.52 ± 4.543** |

As compared to the positive control group,
*p < 0.05,
**p < 0.01,
***p < 0.001,
mean ± standard deviation, and the sample number ≥10.

TABLE 11

| Concentration of brazilin (μM) | Number of lymphocytes (×10⁴) |
|---|---|
| Negative control | 0.09375 ± 0.03786 |
| Positive control | 0.8951 ± 0.4381 |
| Low dose | 0.7421 ± 0.2902 |
| High dose | 0.8106 ± 0.3015 |

TABLE 12

| Concentration of brazilin (μM) | Number of neutrophils (×10⁴) |
|---|---|
| Negative control | 0.0500 ± 0.03371 |
| Positive control | 0.3248 ± 0.1675 |
| Low dose | 0.6476 ± 0.2759 |
| High dose | 0.2178 ± 0.1799 |

Figure 10:
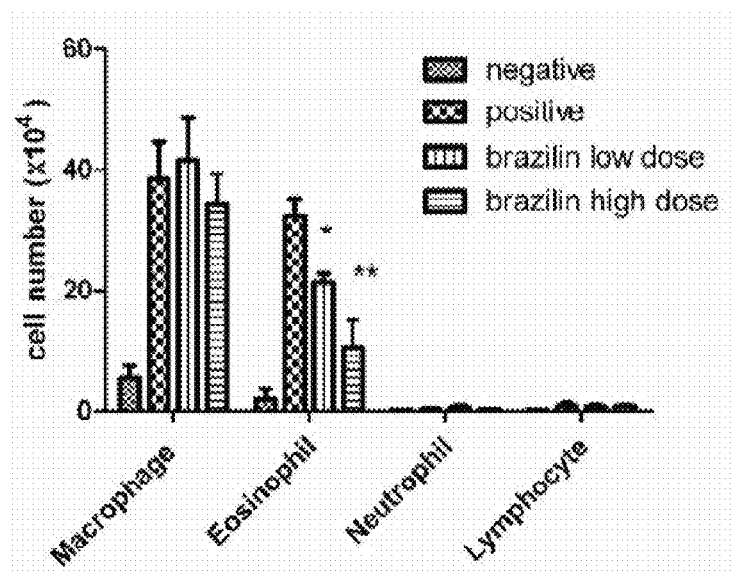
FIG. 10 shows a statistical histogram of various immunocytes in bronochial alveolar lavage fluids of BALB/c mice.

As can be seen from Table 10 and FIG. 10, brazilin decreased the number of eosinophils in the lungs of the mice, indicating that it can inhibit the immune responses of Th2 cells. In addition, as can be seen from FIG. 11, brazilin reduced the invasion of inflammatory cells, and thus it can inhibit the inflammatory reactions.

Experiment F: Cytokine Analysis

The bronchial alveolar lavage fluid collected in Experiment E was centrifuged at 4° C. and with a revolution speed of 400 g for 10 minutes. After the supernatant was collected, the expression of eotaxin, IL-4, IL-5, and IFN-γ was analyzed with an ELISA kit (R&D Systems, Inc., USA). The results are shown in Tables 13 to 16 and FIGS. 12 to 15.

TABLE 13

| Concentration of brazilin (μM) | IL-4 concentration (pico-gram/ml) |
|---|---|
| Negative control | 9.302 ± 3.918 |
| Positive control | 75.60 ± 19.04 |
| Low dose | 36.76 ± 5.490* |
| High dose | 23.01 ± 2.327* |

As compared to the positive control group,
*p < 0.05,
**p < 0.01,
***p < 0.001,
mean ± standard deviation, and the sample number ≥10.

TABLE 14

| Concentration of brazilin (μM) | IL-5 concentration (pico-gram/ml) |
|---|---|
| Negative control | 23.68 ± 4.254 |
| Positive control | 100.4 ± 12.38 |
| Low dose | 70.65 ± 6.510* |
| High dose | 52.10 ± 6.223*** |

As compared to the positive control group,
*p < 0.05,
**p < 0.01,
***p < 0.001,
mean ± standard deviation, and the sample number ≥10.

TABLE 15

| Concentration of brazilin (μM) | Eotaxin concentration (pico-gram/ml) |
|---|---|
| Negative control | 4.140 ± 1.204 |
| Positive control | 32.35 ± 2.635 |
| Low dose | 18.64 ± 3.784*** |
| High dose | 12.61 ± 1.334*** |

As compared to the positive control group,
*p < 0.05,
**p < 0.01,
***p < 0.001,
mean ± standard deviation, and the sample number ≥10.

TABLE 16

| Concentration of brazilin (μM) | IFN-γ concentration (pico-gram/ml) |
|---|---|
| Negative control | 4.719 ± 1.398 |
| Positive control | 4.967 ± 1.695 |
| Low dose | 3.598 ± 1.218 |
| High dose | 4.288 ± 0.868 |

As compared to the positive control group,
*p < 0.05,
**p < 0.01,
***p < 0.001,
mean ± standard deviation, and the sample number ≥10.

As can be seen from Tables 13 to 16 and FIGS. 12 to 15, brazilin inhibited the production of IL-4 and IL-5 cytokines of Th2 cells, but had no effect on IFN-γ cytokine of Th1 cells, indicating that brazilin can inhibit excessively high immune responses of Th2 cells in the immunologic balance between the Th1 cells and the Th2 cells, so it can be used for treatment of allergic diseases. In addition, brazilin inhibited the production of β-chemokine, eotaxin, indicating that it can inhibit immune responses of Th2 cells by inhibiting the production of β-chemokine, thereby treating allergic diseases.

Experiment G: Airway Resistance Determination

Airway (pulmonary) resistance determination was carried out by conducting invasive body plethysmography according to the Glaab's method (see Glaab et al., Repetitive measurements of pulmonary mechanics to inhaled cholinergic challenge in spontaneously breathing mice. *J Appl Physiol*, 2004; 97:1104-1111, which is incorporated herein in its entirety by reference). In this method, the increase of pulmonary resistance of mice administrated with methacholine is observed.

First, BALB/c mice were anesthetized with 70 to 90 mg/kg-body weight of pentobarbital sodium (Sigma), and the trachea of the mice were cut to generate a bore, and the mice were subjected to external ventilation (150 breaths/minute) with a ventilator (Harvard Rodent Ventilator, model 683, Southnatick, Mass., USA) controlled by a computer to maintain the tidal volume at 0.3 ml and the terminal expiring positive pressure at 3 to 4 cm-$H_2O$. A PE-50 pipeline was inserted into the gullets and reached to the chest position of the mice, and the pipeline was connected to a pressure transducer (LDS GOULD, Valley View, Ohio, USA), and the pressure, air flow rate, and the variation of air capacity in the lungs of the mice were recorded. Software (Model PNM-PCT100W, LDS PONEMAH Physiology Platform, LDS GOULD) was used to analyze the airway resistance. An atomizer was used to generate methacholine spray, which was then administrated to the mice via the ventilator. The data was obtained by deducting the pulmonary resistance (0.45 cm $H_2O.s.ml^{-1}$) gained by the pipeline inserted into the trachea of the mice, wherein pulmonary resistance RL ratio=RL after methacholine nebulization/RL after PBS nebulization. The results are shown in Tables 17 to 20 and FIG. 16.

TABLE 17

| Concentration of brazilin (µM) | methacholine 3.125 (mg/ml) pulmonary resistance Rrs (cm H$_2$O/ml) |
|---|---|
| Negative control | 1.720 ± 0.2131 |
| Positive control | 3.205 ± 0.3745 |
| Low dose | 2.237 ± 0.1567*** |
| High dose | 2.535 ± 0.1251*** |

As compared to the positive control group,
*p < 0.05,
**p < 0.01,
***p < 0.001,
mean ± standard deviation, and the sample number ≥5.

TABLE 18

| Concentration of brazilin (µM) | methacholine 6.25 (mg/ml) pulmonary resistance Rrs (cm H$_2$O/ml) |
|---|---|
| Negative control | 1.930 ± 0.2508 |
| Positive control | 3.319 ± 0.4910 |
| Low dose | 2.206 ± 0.06650*** |
| High dose | 2.680 ± 0.1676*** |

As compared to the positive control group,
*p < 0.05,
**p < 0.01,
***p < 0.001,
mean ± standard deviation, and the sample number ≥5.

TABLE 19

| Concentration of brazilin (µM) | methacholine 12.5 (mg/ml) pulmonary resistance Rrs (cm H$_2$O/ml) |
|---|---|
| Negative control | 2.118 ± 0.2981 |
| Positive control | 3.806 ± 0.4552 |
| Low dose | 2.432 ± 0.1259*** |
| High dose | 3.247 ± 0.1368*** |

As compared to the positive control group,
*p < 0.05,
**p < 0.01,
***p < 0.001,
mean ± standard deviation, and the sample number ≥5.

TABLE 20

| Concentration of brazilin (µM) | methacholine 25 (mg/ml) pulmonary resistance Rrs (cm H$_2$O/ml) |
|---|---|
| Negative control | 2.306 ± 0.3270 |
| Positive control | 4.120 ± 0.5254 |
| Low dose | 2.869 ± 0.1831*** |
| High dose | 3.691 ± 0.1542*** |

As compared to the positive control group,
*p < 0.05,
**p < 0.01,
***p < 0.001,
mean ± standard deviation, and the sample number ≥5.

Figure 16:
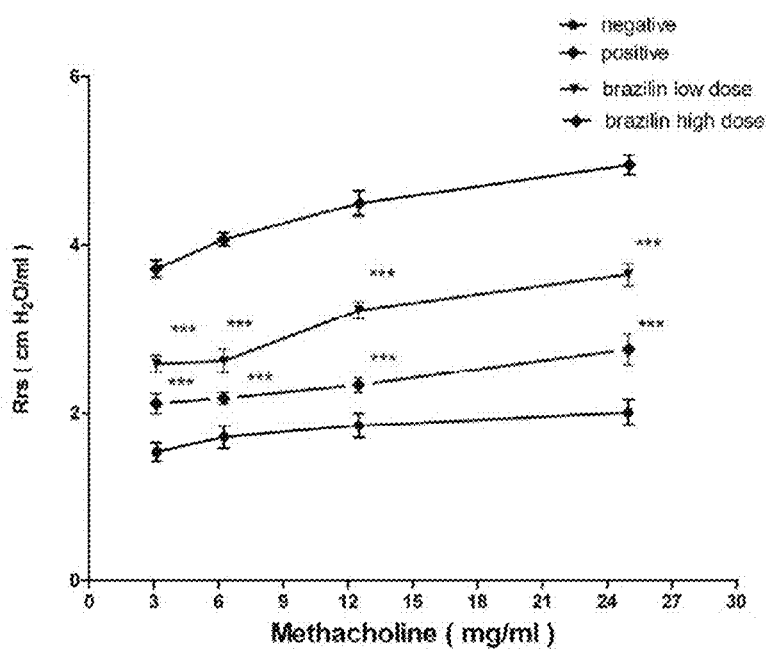
FIG. 16 is a graph of pulmonary resistance determination of the BALB/c mice.

As can be seen from Tables 17 to 20 and FIG. 16, brazilin reduced the airway resistance of the mice, and thus it can be used for treatment of allergic asthma.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A method for treating allergic asthma allergic asthma comprising administrating to a mammal in need thereof an effective amount of an active component selected from a group consisting of a compound of formula (I), its pharmaceutically acceptable salts and esters, and combinations thereof:

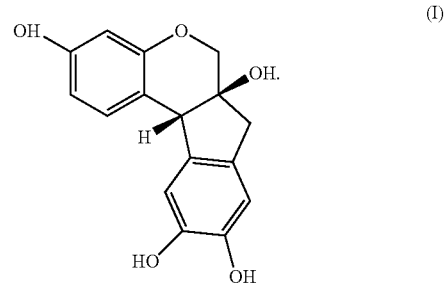 [SMILES: Oc1ccc2c(c1)OC[C@]1(O)Cc3cc(O)c(O)cc3[C@H]21]

2. The method as claimed in claim 1, wherein the active component is administered in an amount effective to inhibit production of the chemokine eotaxin (CCL11).

3. The method as claimed in claim 1, wherein the active component is administered in an amount effective to inhibit airway inflammation or decrease airway resistance.

4. The method as claimed in claim 1, wherein the active component is administered in an amount effective to inhibit the production of at least one of the cytokines Interleukin-4 (IL-4) and Interleukin-5 (IL-5), and/or to inhibit the production of β-chemokine.

* * * * *